US006954663B2

(12) United States Patent
Hall

(10) Patent No.: US 6,954,663 B2
(45) Date of Patent: Oct. 11, 2005

(54) CONTINUOUS WAVE OPTICAL IMAGING ASSUMING A SCATTER-LAW

(75) Inventor: David J. Hall, Montreal (CA)

(73) Assignee: ART Advanced Research Technologies Inc., Saint-Laurent (CA)

( * ) Notice: Subject to any disclaimer, the term of this patent is extended or adjusted under 35 U.S.C. 154(b) by 72 days.

(21) Appl. No.: 10/337,971

(22) Filed: Jan. 7, 2003

(65) Prior Publication Data

US 2004/0133085 A1 Jul. 8, 2004

(51) Int. Cl.[7] ................................................. A61B 5/00
(52) U.S. Cl. ...................... 600/322; 600/473; 600/476
(58) Field of Search ............................... 600/309–310, 600/322, 473, 476

(56) References Cited

U.S. PATENT DOCUMENTS

| | | | | |
|---|---|---|---|---|
| 5,348,003 A | * | 9/1994 | Caro | 600/310 |
| 5,492,118 A | * | 2/1996 | Gratton et al. | 600/316 |
| 5,795,295 A | * | 8/1998 | Hellmuth et al. | 600/407 |
| 6,075,610 A | * | 6/2000 | Ueda et al. | 600/310 |
| 6,195,574 B1 | * | 2/2001 | Kumar et al. | 600/323 |
| 6,263,221 B1 | * | 7/2001 | Chance et al. | 600/310 |
| 6,501,975 B2 | * | 12/2002 | Diab et al. | 600/336 |
| 6,549,284 B1 | | 4/2003 | Cheng et al. | |
| 2002/0190212 A1 | * | 12/2002 | Boas et al. | 250/341.1 |
| 2004/0133085 A1 | * | 7/2004 | Hall | 600/320 |

FOREIGN PATENT DOCUMENTS

EP 0592200 A1 * 4/1994 ............ A61B/5/00

OTHER PUBLICATIONS

Simon R. Arridge et al., Nonuniqueness in diffusion–based optical tomography, Optics Letters, vol. 23, No. 11, Jun. 1, 1998, pp 882–884.

A.J. Berger et al., Broadband absorption spectroscopy by combining frequency–domain and steady–state techniques, Optical Tomography and Spectroscopy of Tissue, Proc. SPIE, vol. 4250, 2001, pp 437–442.

Corlu A. et al., "Uniqueness and wavelenght optimization in continuous–wave multispectral diffuse optical tomography", Optics Letters, Dec. 1, 2003, vol. 28, No. 23, pp. 2339–2341.

Arridge, S. R. et al: "A gradient–based optimisation scheme for optical tomography", Optics Express, Mar. 16, 1998, vol. 2, No. 6, pp. 213–226.

* cited by examiner

Primary Examiner—Eric F. Winakur
Assistant Examiner—Matthew J Kremer
(74) Attorney, Agent, or Firm—Kent Daniels; Ogilvy Renault

(57) ABSTRACT

There is provided a method and a system for determining the concentration of chromophores and reconstructing images in turbid media, such as animal tissues, using a continuous wave optical approach. In particular the approach is based on measurements of attenuation signals and the calculation of concentrations of chromophores using a predetermined scatter law. The system comprises a continuous wave photon migration model calculator coupled to an optical source and detector for estimating concentrations of chromophores and scatter parameters used in image reconstruction.

29 Claims, 1 Drawing Sheet

CONTINUOUS WAVE OPTICAL IMAGING ASSUMING A SCATTER-LAW

CROSS-REFERENCE TO RELATED APPLICATIONS

This is the first application filed for the present invention.

TECHNICAL FIELD

This invention relates to the field of optical imaging. More specifically the invention relates to the field of optical imaging of homogeneous or inhomogeneous turbid media such as biological tissue using continuous wave (CW) measurements.

BACKGROUND OF THE INVENTION

The field of biomedical optics has witnessed rapid growth over the last decade. The advent of new technology has permitted the development of time point spread function (TPSF)-based approaches which enable measurements to decouple the attenuation coefficient into absorption and scattering coefficients. This is beyond the fundamental limit of continuous wave approaches whose measurements only yield the attenuation coefficient.

Measurements of absorption of chromophores within tissues is a very valuable source of information since spectroscopic analysis of the tissue absorption spectrum permits the chromophore concentrations to be determined. Analysis of the chromophore concentrations can in turn yield physiological information and therefore provide a more medically useful image. TPSF based approaches are well suited for extracting absorption coefficients but the approach relies on expensive and complex hardware and software in order to perform the TPSF-based measurements.

It is recognized that CW techniques are less expensive and simpler than the TPSF-based approach. However, it is well-known that the CW approach can only measure the attenuation coefficient and cannot decouple this into the absorption and scattering coefficients. This non-uniqueness problem for CW has been demonstrated mathematically by Arridge et al. (Optics Letters Vol. 23, No. 11, 1998 pp 882–884). The inability of CW to measure the absorption coefficient and only provide the attenuation coefficient is considered to be a contributory reason for the clinical poor performance of previous CW breast imaging attempts.

One approach to circumvent the non-uniqueness of CW is to simply assume that the scattering coefficient is known a priori. However, such assumptions for the scattering coefficient are simply best "guesstimates" and its implementation has not been demonstrated to be clinically viable. Particularly since the scattering coefficient for even very similar tissues (such two breasts of the same patient) can vary widely and its value is not homogenous for a given tissue.

Tromberg et al (Proc. SPIE Vol. 4250 pp 437–442), have developed a TPSF-based approach in the frequency domain in order to measure the absorption and scattering coefficients of a selected type of tissue providing a homogenous medium at a few near infrared (NIR) wavelengths. By assuming a law for scattering coefficient versus wavelength, they derive the scattering coefficient over a wide wavelength range by fitting this law to the scattering coefficients at the few wavelengths measured by the TPSF-based approach. This is different than actually measuring the scattering coefficient over the complete wavelength range and therefore avoids the long acquisition time of TPSF-based information at all wavelengths of interest. A CW approach is then used to derive the attenuation coefficient over this wavelength range.

By using the attenuation coefficient from the CW approach, a few measured scattering coefficients from the TPSF-based approach, and many derived values for scattering coefficient from the scatter-law, values for the absorption coefficient over the complete wavelength range can be calculated to fully characterize the homogenous medium, namely to obtain its absorption coefficient spectrum and its scattering coefficient spectrum that follows a scatter law. This extra absorption coefficient information is considered to yield better estimates of the tissue chromophore concentrations than that provided by the few absorption coefficients measured by the TPSF-based approach alone.

Tromberg et al. have only used this approach for global/localized spectroscopy where the tissue region of interest is assumed to be homogeneous. Furthermore, their approach still requires the acquisition of TPSF based optical measurements in addition to the continuous wave measurements.

Thus, there is a need for an improved method for estimating concentrations of chromophores within tissue.

SUMMARY OF THE INVENTION

In accordance with one embodiment of the present invention, a method and system for modeling an attenuation signal arising from the attenuation of a light beam injected into biological tissue is provided. The method allows for the determination of concentrations of chromophores within the tissue without the need of acquiring time point spread function (TPSF) based information.

In one aspect there is provided a method for determining concentration of one or more chromophores in a turbid medium the method comprising: measuring an attenuation signal using continuous wave (CW) at a predetermined number of wavelengths; providing a scatter law in which scatter is a function of wavelength; estimating scatter parameters of the provided scatter law and a concentration for the one or more chromophores, the chromophores having a predetermined relationship between chromophore absorption and concentration as a function of wavelength; calculating attenuation values at the predetermined wavelengths using the estimated concentrations and scatter parameters; adjusting the concentration for the one or more chromophores and the scatter parameters until the calculated attenuation values and the measured attenuation differ by less than a predetermined value thereby determining the concentration within the medium; and wherein the predetermined number of wavelengths is sufficient to provide a desired degree of accuracy in the determination of the concentration.

In a further aspect there is provided a method for optical imaging of a region of interest in a turbid medium, the method comprising: injecting light at a predetermined number of wavelengths into the tissue at one or more injection ports; detecting the light at one or more detection ports to obtain a measured attenuation function; providing a scatter law; estimating a concentration for one or more chromophores and scatter parameters at a plurality of voxels in the region of interest; calculating attenuation values at the predetermined number of wavelengths using the estimated concentration and scatter parameters and a photon diffusion equation to generate a calculated attenuation function; adjusting the concentration and the scatter parameters until the calculated attenuation function and the measured attenuation function differ by less than a predetermined value; generating an image of the tissue using the adjusted concentration for the one or more chromophores at the plurality of voxels in the region of interest; and wherein a plurality of injection ports/detection ports configurations are used to measure the attenuation function.

In yet another aspect there is provided a system for Continuous Wave optical imaging of a turbid medium, the system comprising: at least one optical source for providing continuous optical energy; at least one optical detector for detecting optical energy and generating continuous data; a source/object optical coupling for coupling the optical source to a desired position on the object; a detector/object optical coupling for coupling the optical detector to a desired position on the object; an acquisition controller connected to the optical source and the optical detector for collecting the continuous data for a plurality of source/detector geometries within a region of interest in the object; a continuous-wave photon migration model calculator for calculating attenuation values; and an estimator using the continuous data and the calculated values to estimate optical properties of the object.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

Figure 1:
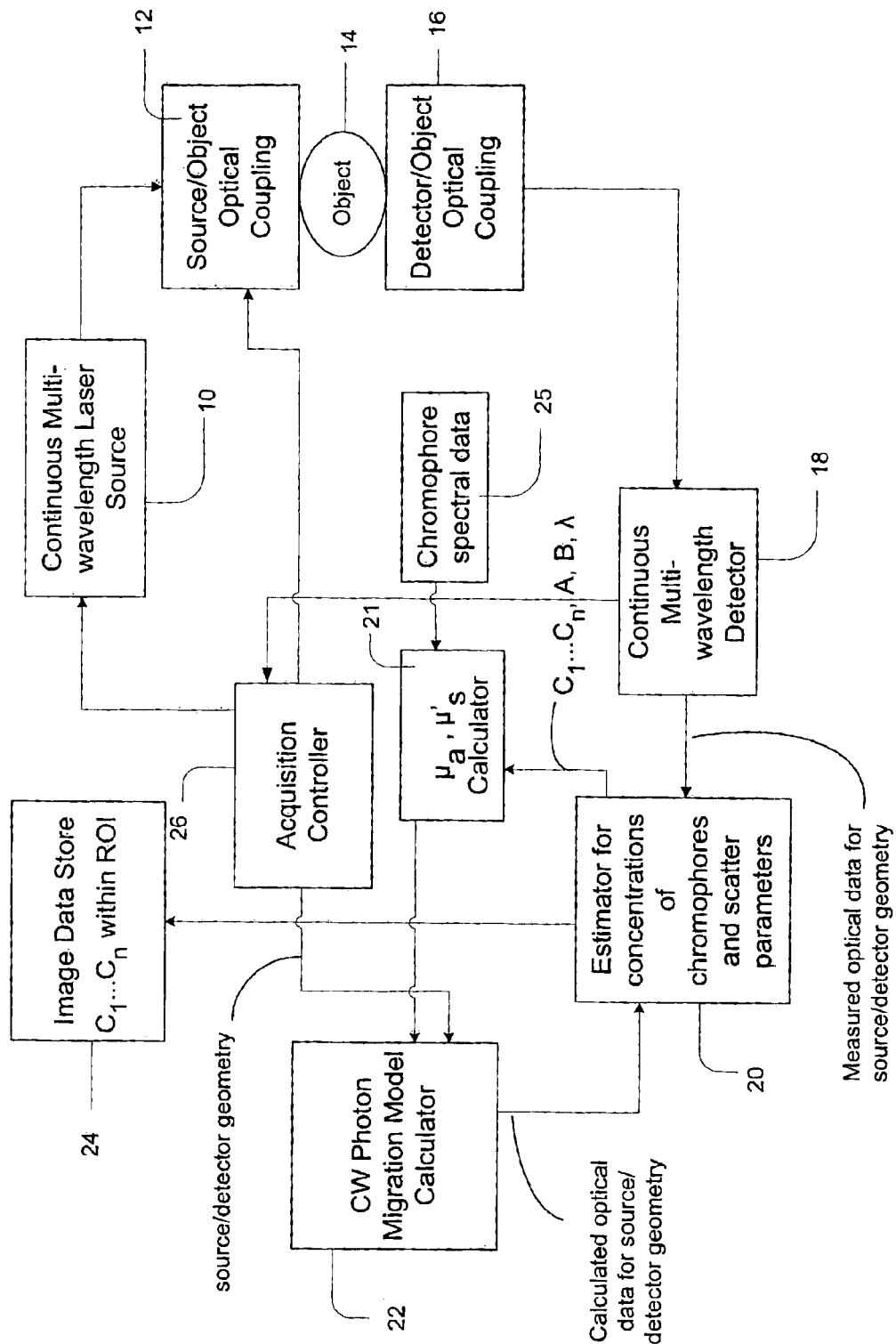
FIG. 1 illustrates a flow chart diagram of an embodiment of the optical system in accordance with the invention.

In accordance with one embodiment of the present invention, a method for modeling an attenuation signal arising from the attenuation of a light beam injected into biological tissue is provided. The method allows for the determination of concentrations of chromophores within the tissue without the need of acquiring time point spread function (TPSF) based information.

In another aspect, the method in accordance with the invention allows scatter parameters of the tissues to be estimated.

The integrated intensity of light injected into an object such as biological tissue is reduced as a result of absorption ($\mu_a$) by chromophores as well as scattering ($\mu_s'$) within the object. Both processes are wavelength dependent. The detected attenuation signal, $ATT(\lambda)$, is therefore also a function of the wavelength and can be approximated by the following relationship:

$$ATT(\lambda) = f[\mu_a(\lambda), \mu_s'(\lambda)] \quad (1)$$

The concentration of a chromophore within a scattering medium is given by:

$$\mu_a(\lambda) = \alpha(\lambda)c \quad (2)$$

Where $\alpha$ is a coefficient, specific to each chromophore, that incorporates the dependency of the absorption on the scattering and c is the concentration of the chromophore. In a tissue comprising a large number of different type of molecules, the absorption at each wavelength is the sum of the absorption due to each chromophore i. The chromophores can be either endogenous or exogenous or a combination of both.

$$\mu_a(\lambda) = \sum_i \mu_{ai}(\lambda) \quad (3)$$

$$\mu_a(\lambda) = \sum_i \alpha_i(\lambda)c_i \quad (4)$$

As mentioned above, CW measurements cannot distinguish between the absorption and scatter components of the attenuation value preventing the direct calculation of the concentration.

In the present invention the concentration of chromophores is estimated using a measured attenuation value obtained in CW mode and assuming a given scatter law. In a preferred embodiment the scatter law is assumed to be of the form $A\lambda^{-B}$. Previous scatter laws with wavelength dependence are known such as Lord Rayleigh's where $B=-4$ and applies when the particle size is much smaller than the wavelength. Later, Gustav Mie developed a more general theory for spherical particles of arbitrary size, r. Although neither laws are directly applicable to biological tissue it seems preferable to choose a scatter law of the general functional form $A\lambda^{-B}$. Taking this scatter law into consideration, equation (1) thus becomes eq. (5):

$$ATT(\lambda) = \frac{S_o}{4\pi Dr} \exp(-kr) \quad (5)$$

Where $$D = \frac{1}{3(\mu_s' + \mu_a)} \text{ and } k = \left(\frac{\mu_a}{D}\right)^{1/2}$$

And where $$\mu_a = \alpha_i c_i \text{ and } \mu_s' = A\lambda^{-B}$$

In the case of a homogeneous infinite medium the attenuation is a function of $\lambda$ (as per eq. 1) and eq. 5 can be written as $$ATT(\lambda) = \frac{S_o}{4\pi r} 3(A\lambda^{-B} + \alpha_i(\lambda)c_i) \exp[-(3\alpha_i(\lambda)c_i(A\lambda^{-B} + \alpha i(\lambda)c_i)]^{1/2} r$$

Using this form, the variables A, B and $c_i$ are estimated and adjusted until the difference between the calculated and measured attenuation value is less than a predetermined value. In a preferred embodiment the coefficients $\lambda_i$ are known for the chromophores of interest determining substantially the optical properties of the object being imaged. Also, it is preferred that all the chromophores substantially contributing to the absorption signal are included in the estimation.

It will be appreciated that the estimation of the concentration of the chromophores should be effected at plurality of wavelengths to provide a reliable estimate of the concentrations, $c_i$, as well as the scatter law coefficients, A and B. A predetermined number of wavelengths may be selected based, for example, on the spectral behavior of each chromophore to optimize the sensitivity of the calculation to each chromophore.

The method described above can be advantageously used for estimating the spatial distribution of concentration of chromophores in non-homogeneous media such as animal tissues. This distribution can be converted into a medical image.

The attenuation of the intensity of light within an inhomogeneous medium can be described by photon diffusion equations that are well known in the art, which relate the attenuation and the spatial distribution of absorption $\mu_a$ and the scatter coefficient $\mu_s'$.

A region of interest (ROI) within the tissue can be represented by a three dimensional grid with j voxel elements. The image of the ROI can be reconstructed by estimating the concentration c of one or more chromophores for each voxel element j. The concentrations $c_i$ are estimated based on CW measurements at a predetermined number of wavelengths to provide attenuation values, a predetermined scatter law and on a photon diffusion equation.

In a first step, the concentration c of at least one chromophore and the scattering parameters A and B are set to initial values for all elements j of the grid. The selected concentration and scatter parameters can be based on known average values for similar tissue. Alternatively, the measured attenuation function can be compared with a bank of attenuation functions for similar tissues to find a "best match" and using the corresponding concentrations values for chromophores and scatter parameters. Based on these initial values, $\mu_a$ and $\mu_s'$ are calculated for each voxel element j. The photon diffusion equation can then be used to calculate the attenuation at each of the predetermined wavelengths for the selected detector positions. The calculated and measured attenuation values are then compared and the $c_i$ and A and B can be adjusted until the difference between the measured and calculated attenuation is less than a predetermined value.

It will be appreciated that the above method can be modified without departing from the scope of the invention. For example, the scatter parameters A and B may be restricted to a constant value while $c_i$ are modified until the calculated attenuation converges to a predetermined value at which point A and B may then be modified and the process repeated until final convergence value is obtained. Other optimization algorithms, as would be apparent to one skilled in the art are also possible.

Preferably the calculation of $\mu_a$ using $c_i$ is based on a predetermined equation defining their relationship. In particular this equation may comprise chromophore and wavelength specific coefficients.

The variable parameters, that is the concentration of the chromophores and the scatter parameters, of each grid element can be adjusted using a minimization fitting approach until the difference between the calculated and the measured attenuation functions reaches a predetermined value. In a preferred embodiment, the attenuation function is reconstructed using an inhomogeneous model of light propagation where the problem is minimized until the solution of the equation approaches the experimental attenuation function. This provides the coefficient for the concentration of the chromophores and the scattering parameters within each voxel from which the image of the tissue can be reconstructed.

Examples of chromophores may include but ate not limited to oxyhemoglobin, deoxyhemoglobin, water, and lipid.

In a preferred embodiment the concentrations $c_i$ are constrained to ranges of values compatible with the tissue being analyzed, i.e. physiologically realistic. Similarly the scattering parameters can be constrained to a range of expected realistic values which are known a priori, such as from TPSF-based measurements.

In a preferred embodiment the concentration of at least 4 chromophores is estimated and adjusted.

The method of the present invention uses attenuation measurements of a continuous wave light source injected at a plurality of wavelengths into a tissue to reconstruct an optical image of the tissue. With reference to FIG. 1, an embodiment of a system used to obtain attenuation measurements light transmitted through a tissue is shown. Light generated by source 10 is injected at one or more injection ports provided by the source/object optical coupling 12 and travels through the object 14, which can be animal tissue while being scattered and absorbed and exits the tissue to be detected at one or more collection ports provided by detector/object optical coupling 16. The source/object and detector/object optical coupling can be fibre optics, free space optic or any combination thereof. In the case of free space optics, mirrors can be used to directionally propagate the light so that the light can be injected and collected from desired areas of the object. It will appreciated that the mirrors can be driven by Galvanometers. Injection and collection may be achieved using optical fibers for example. Furthermore the above-mentioned optical couplings may comprise a plurality of fibre optics, as well as optical switches to allow the selection of desired fibre optics for light injection and detection. The geometry of the injection and detection ports relative to the region of interest in the tissue is optimized for parameters such as sensitivity, signal intensity and the like and preferably involves a plurality of source/detector configurations. In particular, the configuration of the injection/detection port combination could depend on the chromophores that are used to obtain the image. Light exiting is detected at detector 18 to produce an optical signal that is used to generate attenuation values.

Acquisition controller 26 is used to adjust the optical source intensity as a function of the detected optical energy for optimizing signal to noise ratio. It will be appreciated that a broadband light source can be detected by a simultaneous multi-wavelength detector so as to inject and detect light simultaneously for a given source-detector geometry. Data acquisition is greatly accelerated by such a system configuration. Of course, as will be apparent to a person skilled in the art, many configurations are possible. Light can be injected at one wavelength at a time and detected using a detector that is not wavelength selective. Alternatively light can be injected using a broadband source and detected using a spectrometer or filter that detects one selected wavelength at a time.

A 2D or 3D image processing and display system (not shown) reads the image data from store 24 for displaying a reconstituted image of the tissue or other turbid medium.

Chromophore concentrations and scatter parameters are estimated in estimator 20 using predetermined criteria. The estimated concentrations and parameters are then used to calculate $\mu_a$ and $\mu_s'$ (as a function of wavelength) in calculator 21 using the known chromophore spectral data in store 25. The resulting estimated values of $\mu_a$ and $\mu_s'$ (as a function of wavelength) for each voxel are provided to CW photon migration model calculator 22 where calculated attenuation values (as a function of wavelength) are generated using a photon diffusion equation and compared with measured attenuation values (as a function of wavelength) to provide a comparative basis for adjusting the $c_i$, A and B. Once the concentrations, A and B (thus $\mu_a$ and $\mu_s'$ spectra) are determined, they are provided to image data store 24. An acquisition controller 26 is also provided that controls acquisition by determining the wavelengths of acquisition and the source/detector configurations.

The embodiment(s) of the invention described above is (are) intended to be exemplary only. The scope of the invention is therefore intended to be limited solely by the scope of the appended claims.

What is claimed is:

1. A method for determining concentration of one or more chromophores in a turbid medium the method comprising:
    i) measuring an attenuation signal using continuous wave (CW) illumination at a predetermined number of wavelengths;
    ii) providing a scatter law in which scatter is a function of wavelength;
    iii) estimating scatter parameters of said provided scatter law and a concentration for the one or more chromophores, said chromophores having a predetermined relationship between chromophore absorption and concentration as a function of wavelength;
    iv) calculating attenuation values at said predetermined wavelengths using the estimated concentrations and scatter parameters;
    v) adjusting the concentration for the one or more chromophores and the scatter parameters until the calculated attenuation values and the measured attenuation differ by less than a predetermined value thereby determining said concentration within said medium; and
    wherein said predetermined number of wavelengths is sufficient to provide a desired degree of accuracy in said determination of said concentration.

2. The method as claimed in claim 1 wherein said scatter parameters are maintained constant during said step of adjusting said concentration of said one or more chromophores.

3. The method as claimed in claim 1 wherein the general form of the scatter law is given by $A\lambda^{-B}$.

4. The method as claimed in claim 1 wherein said estimations of said concentration of one or more chromophores and said scatter parameters are based on known concentrations and scatter parameters in similar turbid media.

5. The method as claimed in claim 1, wherein the estimation of the concentrations and the scatter parameters is based on a comparison of the measured attenuation function with previously calculated attenuations functions for turbid media substantially identical to said turbid medium.

6. The method as claimed in claim 1 wherein the concentration of the one or more chromophores is inhomogeneous within said turbid medium and wherein the attenuation values are calculated using a photon diffusion equation.

7. A method for optical imaging of a region of interest in a turbid medium, said method comprising:
    i) injecting light at a predetermined number of wavelengths into said tissue at one or more injection ports;
    ii) detecting said light at one or more detection ports to obtain a measured attenuation function;
    iii) providing a scatter law;
    iv) estimating a concentration for one or more chromophores and scatter parameters at a plurality of voxels in said region of interest;
    v) calculating attenuation values at said predetermined number of wavelengths using the estimated concentration and scatter parameters and a photon diffusion equation to generate a calculated attenuation function;
    vi) adjusting said concentration and said scatter parameters until said calculated attenuation function and said measured attenuation function differ by less than a predetermined value;
    vii) generating an image of said tissue using the adjusted concentration for said one or more chromophores at the plurality of voxels in the region of interest; and
    wherein a plurality of injection ports/detection ports configurations are used to measure said attenuation function.

8. The method as claimed in claim 7 wherein said scatter parameters are maintained constant during said step of adjusting said concentration of said one or more chromophores.

9. The method as claimed in claim 7 wherein the general form of the scatter law is given by $A\lambda^{-B}$.

10. The method as claimed in claim 9 wherein the chromophores are endogenous and are selected from: oxyhemoglobin and deoxyhemoglobin.

11. The method as claimed in claim 7 wherein said estimations of said concentration of one or more chromophores and said scatter parameters are based on known concentrations and scatter parameters in similar tissues.

12. The method as claimed in claim 7, wherein the estimation of the concentrations and the scatter parameters is based on a comparison of the measured attenuation function with previously calculated attenuation functions for tissues substantially identical to said tissue.

13. The method as claimed in claim 7 wherein the concentration of the one or more chromophores is inhomogeneous within said tissue and wherein the attenuation values are calculated using a photon diffusion equation.

14. The method as claimed in claim 7 wherein the chromophores are selected from endogenous and exogenous chromophores.

15. A system for continuous wave optical imaging of animal tissue, the system comprising:
    at least one optical source for providing continuous optical energy at a plurality of wavelengths;
    at least one optical detector for detecting optical energy and generating continuous data;
    a source/object optical coupling for coupling said optical source to a desired position on said tissue;
    a detector/object optical coupling for coupling said optical detector to a desired position on said tissue;
    an acquisition controller connected to said optical source and said optical detector for collecting said continuous data for a plurality of wavelengths and a plurality of source/detector geometries within a region of interest in said tissue;
    a continuous-wave photon migration model calculator for calculating attenuation values;
    an estimator using said continuous data and said calculated values to estimate concentration of at least one known chromophore having a known absorption spectrum and wavelength dependent scatter properties;
    an optical diffusion parameters calculator using said estimated concentration and scatter properties and chromophore spectral data to calculate absorption and scatter coefficients for said tissue.

16. The system as claimed in claim 15 further comprising a chromophore spectral data store for providing chromophore specific absorption coefficients to said optical diffusion parameters calculators.

17. The system as claimed in claim 15 wherein said source comprises one or more laser source.

18. The system as claimed in claim 15 wherein said source/object and detector/object optical couplings for coupling said optical source and said optical detector with said object are selected from fiber optics, free-space optics and a combination thereof.

19. The system as claimed in claim 18 wherein said source/object and said detector/object optical couplings are free-space optics and wherein said free-space optics comprise mirrors to directionally propagate light so that the light is injected and collected from desired areas on said object.

20. The system as claimed in claim 19 wherein said mirrors are galvanometers-driven mirrors.

21. The system as claimed in claim 18 wherein said source/object and said detector/object optical couplings comprise a plurality of fiber optics and optical switches to select desired fiber optics for light injection and detection.

22. The system as claimed in claim 15 wherein said source/object optical couplings comprise a plurality of light injection ports and collection ports for coupling said optical source and said optical detector respectively with said tissue.

23. The system as claimed in claim 15 wherein said optical source provide optical energy at a plurality of wavelengths simultaneously.

24. The system as claimed in claim 23 wherein said optical detector detects optical energy at a plurality of wavelengths simultaneously.

25. The system as claimed in claim 15 wherein said acquisition controller is used to adjust said optical source intensity as a function of said detected optical energy for optimizing signal to noise ratio.

26. The system as claimed in claim 15 further comprising a display for displaying a reconstituted image of said tissue.

27. The system as claimed in claim 15 wherein said calculation of said scatter coefficient is based on a predetermined scatter law.

28. The system as claimed in claim 15 further comprising means for selecting one or more detection wavelength.

29. The system as claimed in claim 28 wherein said means for selecting is a filter.

* * * * *